(12) United States Patent
Putz (10) Patent No.: US 6,656,152 B2
(45) Date of Patent: Dec. 2, 2003

(54) DRUG DELIVERY CATHETER ASSEMBLY WITH INFLATABLE BALLOON

(75) Inventor: David A. Putz, Franksville, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 0 days.

(21) Appl. No.: 09/993,203

(22) Filed: Nov. 16, 2001

(65) Prior Publication Data

US 2003/0097116 A1 May 22, 2003

(51) Int. Cl.⁷ .................. A61M 29/00; A61M 31/00
(52) U.S. Cl. ............... 604/96.01; 604/513; 604/510
(58) Field of Search ............... 604/96.01, 500, 604/510, 513, 103.03, 164.01, 506; 606/192, 193, 194, 196

(56) References Cited

U.S. PATENT DOCUMENTS

| | | | |
|---|---|---|---|
| 4,471,779 A | | 9/1984 | Antoshkiw et al. |
| 4,685,901 A | * | 8/1987 | Parks .................. 604/96 |
| 4,777,951 A | * | 10/1988 | Cribier et al. .......... 128/344 |
| 4,798,586 A | * | 1/1989 | Stevens ................ 604/96 |
| 4,921,478 A | | 5/1990 | Solano et al. |
| 5,033,998 A | | 7/1991 | Corday et al. |
| 5,041,090 A | | 8/1991 | Scheglov et al. |
| 5,505,698 A | | 4/1996 | Booth et al. |
| 5,662,607 A | * | 9/1997 | Booth et al. ............ 604/96 |
| 5,728,066 A | * | 3/1998 | Daneshvar ............. 604/96 |
| 5,792,100 A | * | 8/1998 | Shantha ............... 604/53 |
| 5,792,110 A | | 8/1998 | Cunningham |
| 5,795,331 A | | 8/1998 | Cragg et al. |
| 5,807,328 A | | 9/1998 | Briscoe |
| 5,810,767 A | | 9/1998 | Klein |
| 5,843,022 A | * | 12/1998 | Willard et al. ......... 604/30 |
| 6,017,323 A | | 1/2000 | Chee |
| 6,041,252 A | | 3/2000 | Walker et al. |
| 6,096,021 A | | 8/2000 | Helm et al. |
| 6,120,477 A | | 9/2000 | Campbell et al. |
| 6,146,358 A | | 11/2000 | Rowe |
| 6,203,526 B1 | * | 3/2001 | McBeth et al. ....... 604/96.01 |
| 6,264,633 B1 | | 7/2001 | Knorig |
| 6,283,951 B1 | | 9/2001 | Flaherty et al. |

* cited by examiner

Primary Examiner—Sharon Kennedy
(74) Attorney, Agent, or Firm—Jansson, Shupe & Munger, Ltd (57) ABSTRACT

An improved assembly and method for accurately and safely delivering a drug to a selected intracranial site are disclosed. The assembly ensures delivery of the drug to the selected site by providing a barrier which prevents "backflow" or leakage of the drug. The assembly includes a guide catheter having an inflatable balloon which is able to seal or occlude the tract created by the insertion of the guide catheter into the brain. The guide catheter further includes a passageway which receives a delivery catheter through which the drug is administered to the selected site in the brain. Upon delivery of the drug to the selected site, the balloon may be deflated and the assembly removed.

20 Claims, 7 Drawing Sheets

DRUG DELIVERY CATHETER ASSEMBLY WITH INFLATABLE BALLOON

FIELD OF THE INVENTION

This invention is related generally to the delivery of drugs to a patient and, more particularly, to the intracranial delivery of drugs.

BACKGROUND OF THE INVENTION

The introduction of drugs or other therapeutic agents to sites in the brain is common in many neurosurgical procedures today. Such procedures include the delivery of chemotherapeutic agents such as protein toxins to brain tumors, delivery of genes used in genetic therapy, and the delivery of neural cell or tissue during transplantation surgeries. One area in which use of such procedures is particularly relevant is in drug delivery for treatment of epilepsy and other movement disorders.

In the last twenty years, major advances have been made concerning the identification of specific epileptic syndromes which respond poorly to treatment by ingested drugs but may be successful treated by surgical intervention. Recent advances in diagnostic technology and surgical techniques have led to an increasing use of surgical treatment of epilepsy. In addition, through the discovery that particular seizures result from particular neuronal activity, the targeting of the causal neuronal activity for treatment by antiepileptic drugs has achieved success. The neuronal cell populations responsible for such activity may be eliminated through the direct delivery of drugs such as excitotoxins. The elimination of specific epileptic disturbances has allowed people afflicted with epilepsy to be relieved of disabling seizures and the disturbing side-effects of treatment while avoiding the long-term psychosocial consequences of living with an uncontrolled epileptic disorder.

There are several prior art apparatuses which allow for the introduction of drugs or therapeutic agents to selected brain tissue. One such apparatus is disclosed in U.S. Pat. No. 5,554,148. This patent involves a refillable neural implant which attempts to provide a continuous supply of drugs or other factors to the brain and other tissues at a controlled rate. Such a continuous supply is intended to compensate for deficits in secretions by the patient's improperly functioning source cells. The disclosed device requires the permanent or long-term presence within the brain of the cell chamber which receives and disperses the drugs. Such a presence is not desirable if proper treatment can be achieved without it.

Another prior art device is described in U.S. Pat. No. 5,006,122 which discloses a brain tissue transplantation method utilizing a cannula within a cannula assembly. The first cannula is of the large bore type and is fixed to a stereotactic holding apparatus to allow for its insertion into the brain to the transplant site. The second cannula, which carries donor tissue and a stylet which is used to expel the tissue from the second cannula, is guided within the lumen of the first cannula to the transplant site. The tissue is then transplanted into the brain by withdrawing the first and second cannulas while the stylet within the second cannula is maintained in a fixed position. The stylet is later removed, leaving only the transplanted tissue in the patient.

The '122 device does not provide for reliable delivery of small volumes of matter to a selected site in a patient. Small volumes of fluid injected from the '122 instrument tend to adhere to the surface area of the cannula and flow up around the outside wall of the guide cannula.

U.S. Pat. No. 5,792,110 attempted to overcome this problem. It discloses a cannula within a cannula assembly for delivery of therapeutic agents within a patient's brain. The assembly includes a rigid guide cannula for penetrating a selected site at a predetermined depth and a flexible delivery cannula for delivering the therapeutic agent at the site. The assembly attempts to overcome the problem of injected fluid flowing up the tract created by the insertion of the guide cannula by utilizing a delivery catheter having a much smaller diameter than the guide cannula. It is also disclosed that the delivery cannula is deflected by the guide cannula so that it enters brain tissue at a transverse angle with the guide cannula tract. While an improvement over the prior art, these methods of intracranially delivering therapeutic agents present additional problems, are not easy to use and do not fully prevent the flow of the agents out of the cannula tract.

Therefore, there is a continuing significant need in the field of intracranial drug delivery, particularly involving the introduction of cannulas or catheters into the interior of the brain, for improvements in accuracy and effectiveness of drug delivery, while retaining ease of use. An improved device achieving these goals would improve treatment of the disorders and diseases noted above.

OBJECTS OF THE INVENTION

It is an object of the invention to provide an improved intracranial drug delivery device which ensures delivery to the selected site.

Another object of the invention is to provide an intracranial drug delivery device which is simple in structure and operation in order to facilitate effective drug delivery.

Another object of the invention is to provide an intracranial drug delivery device which allows for precise drug delivery to selected brain tissue while avoiding extensive trauma to and scarring of brain tissue.

Another object of the invention is to provide an intracranial drug delivery device including a guide catheter having an inflatable balloon to seal or occlude the tract created during insertion into the brain.

Another object of the invention is to provide a method of accurately delivering a drug to selected tissue in a patient's brain which minimizes injury to the brain.

Still another object of the invention is to provide a method of safely delivering a drug to selected tissue in a patient's brain through use of an assembly including two catheters.

Yet another object of the invention is to provide a method of ensuring delivery of a drug to a selected site in a patient's brain through use of a guide catheter having an inflatable balloon to seal the catheter tract.

These and other objects of the invention will be apparent from the following descriptions and from the drawings.

SUMMARY OF THE INVENTION

This invention is an improved assembly for effectively delivering a drug to a patient's brain and methods of use thereof. The invention represents a significant advance over the state of the art by providing novel elements, including an inflatable balloon which is able to seal or occlude the catheter tract without damaging the surrounding brain tissue.

The assembly includes a guide catheter and delivery catheter which cooperate to allow for precise drug delivery. The guide catheter has proximal and distal ends, proximal and distal openings and a passageway which extends from one opening to the other. It also includes at least one lumen which extends from the proximal end to the distal end where it terminates at and is in communication with an inflatable balloon.

The delivery cannula is receivable within the passageway of the guide cannula through the proximal end so that it may be guided to the selected site for drug delivery. The delivery catheter has a first opening at its first end and at least one second opening at its second end. The second opening is preferably positioned within the brain adjacent to or near the selected site. An axial bore extends between the first and second opening and provides a path for the drug to reach the selected site in the patient's brain.

The balloon is inflated to seal or occlude the catheter tract, thereby preventing the drug from leaking or "backflowing" away from the selected site. This enables the drug to be fully absorbed by the brain tissue at the selected site to permit proper medical treatment. The balloon is located on the outside of the guide cannula and is separated from the passageway so that it does not protrude into the passageway during inflation. The balloon is preferably deflatable to enable removal of the assembly from the brain after drug delivery to the selected site.

In a preferred embodiment, the second opening of the delivery catheter extends beyond the distal opening of the guide catheter when the delivery catheter is inserted into the passageway. The passageway is preferably slightly larger than the delivery catheter to facilitate insertion of the delivery catheter into the passageway. It is also preferred that the second opening is coaxial with the bore.

An alternative embodiment provides that the second opening of the delivery catheter include multiple openings for delivering the drug to the selected site. These openings need not be coaxial with the bore.

The assembly preferably includes a stylet which is receivable within the passageway for use during insertion of the guide catheter into the brain. The stylet is preferably rigid to allow for precise positioning of the guide catheter inside the brain.

The preferable delivery catheter includes a hub at its first end to facilitate movement of the delivery catheter with respect to the guide catheter.

The invention also includes a method of using the inventive assembly to deliver a drug to a selected site in a patient's brain. The method comprises: inserting into the brain the guide catheter such that the distal opening is near or just short of the selected site; inflating the balloon therein by injecting air through the lumen so that a tract created by the insertion of the guide catheter into the brain is sealed; inserting into the passageway through the proximal opening a delivery catheter; administering the drug to brain tissue at the selected site by passing the drug through the bore; deflating the balloon; removing the delivery catheter from the brain; and withdrawing the guide catheter from the brain.

It is preferable that a stylet is positioned within the passageway during insertion of the guide catheter into the brain and that the stylet is removed from the passageway through the proximal opening before the delivery catheter is inserted.

In one embodiment of the inventive method magnetic resonance imaging (MRI) is preferably utilized to aid the placement of the guide catheter in the brain. Therefore, in this embodiment it is preferred that the stylet be of MRI compatible material such as tungsten.

It is also preferred that the second opening of the delivery catheter extend beyond the distal opening after the delivery catheter is inserted into the guide catheter so that it is adjacent the selected site. It is further preferred that the delivery catheter and guide catheter are removed from the brain simultaneously. Furthermore, the deflating step is preferably performed after the drug has been substantially absorbed by brain tissue at the selected site.

In the preferred embodiment, the balloon is inflated before the delivery cannula is inserted into the passageway. In an alternate embodiment, the balloon is inflated after the delivery cannula is inserted into the passageway.

Another method of use of the inventive assembly to ensure effective drug delivery at a selected site in a patient's brain comprises: preparing for insertion into the brain the guide catheter; positioning in the passageway a stylet to prevent brain matter from entering the passageway upon insertion of the guide catheter into the brain; inserting into the brain the guide catheter and stylet; removing the stylet from the passageway; inflating the balloon by injecting air through the lumen so that a tract created by the insertion of the guide catheter into the brain is occluded; inserting into the passageway the delivery catheter; administering the drug to brain tissue at the selected site by passing the drug through the bore; deflating the balloon after the drug is substantially absorbed by the brain tissue at the selected site; removing the delivery catheter from the brain; and withdrawing the guide catheter from the brain.

DETAILED DESCRIPTION OF PREFERRED EMBODIMENTS

Figure 1:
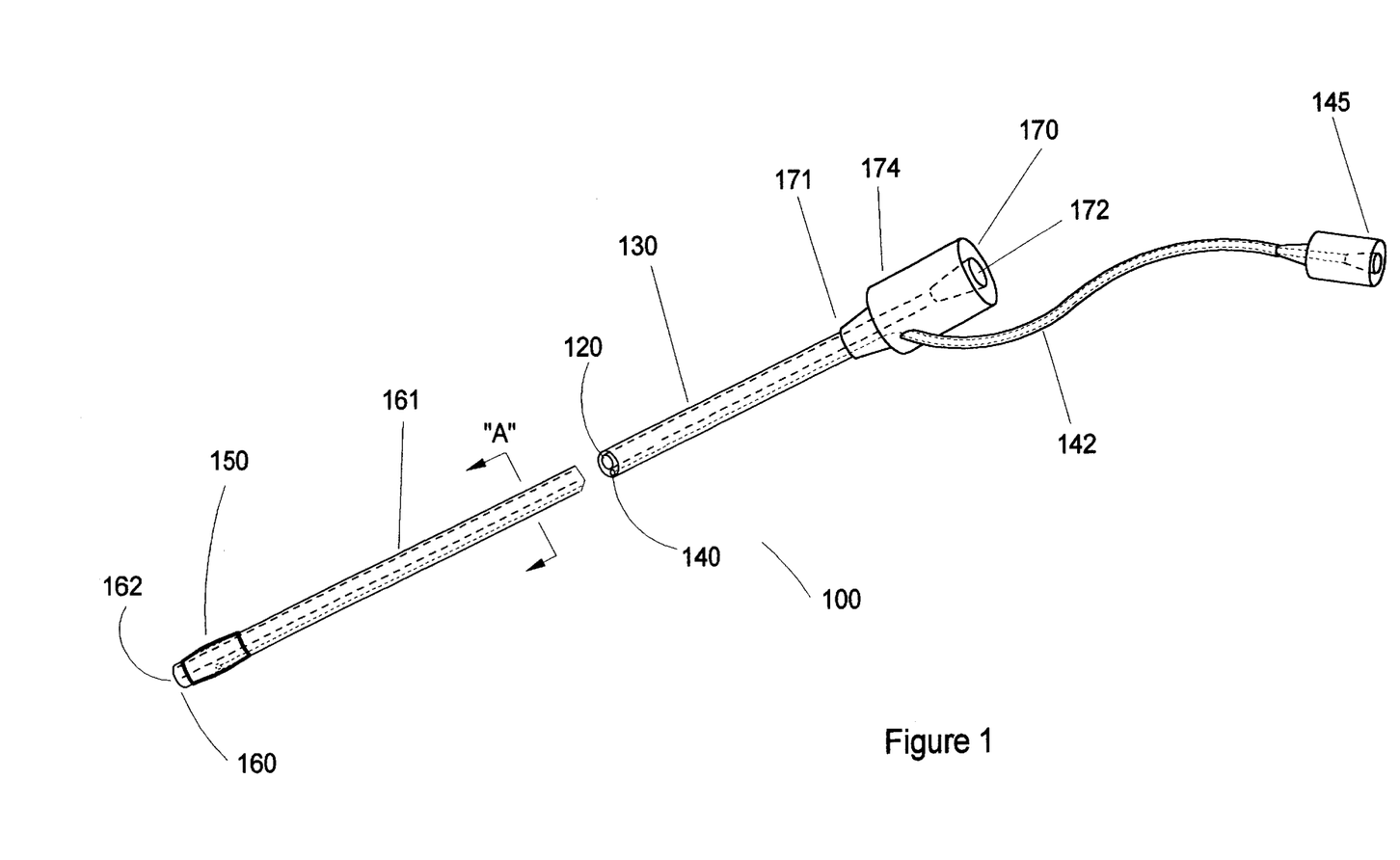
FIG. 1 is a perspective view of the guide catheter of the invention with a cut-away section to depict internal features.

FIG. 1 is a perspective view of the guide catheter 100 of the invention with a cut-away section to depict internal features. Guide catheter 100 is comprised of a shaft 130 and hub 174. Hub 174 is located at the proximal end 170 and shaft 130 extends from proximal end 170 to distal end 160. Shaft 130 is preferably polyimide and hub 174 is preferably plastic. Passageway 120 passes through both shaft 130 and hub 174 to connect distal opening 162 and proximal opening 172. Lumen 140 extends alongside passageway 120 from balloon 150 to air feed tube 142. Lumen 140 is operatively connected to balloon 150 to allow air to be injected through lumen injection port 145 and air feed tube 142 to inflate balloon 150. Balloon 150 is preferably an elastomer and air feed tube 142 is preferably polyurethane.

Figure 2:
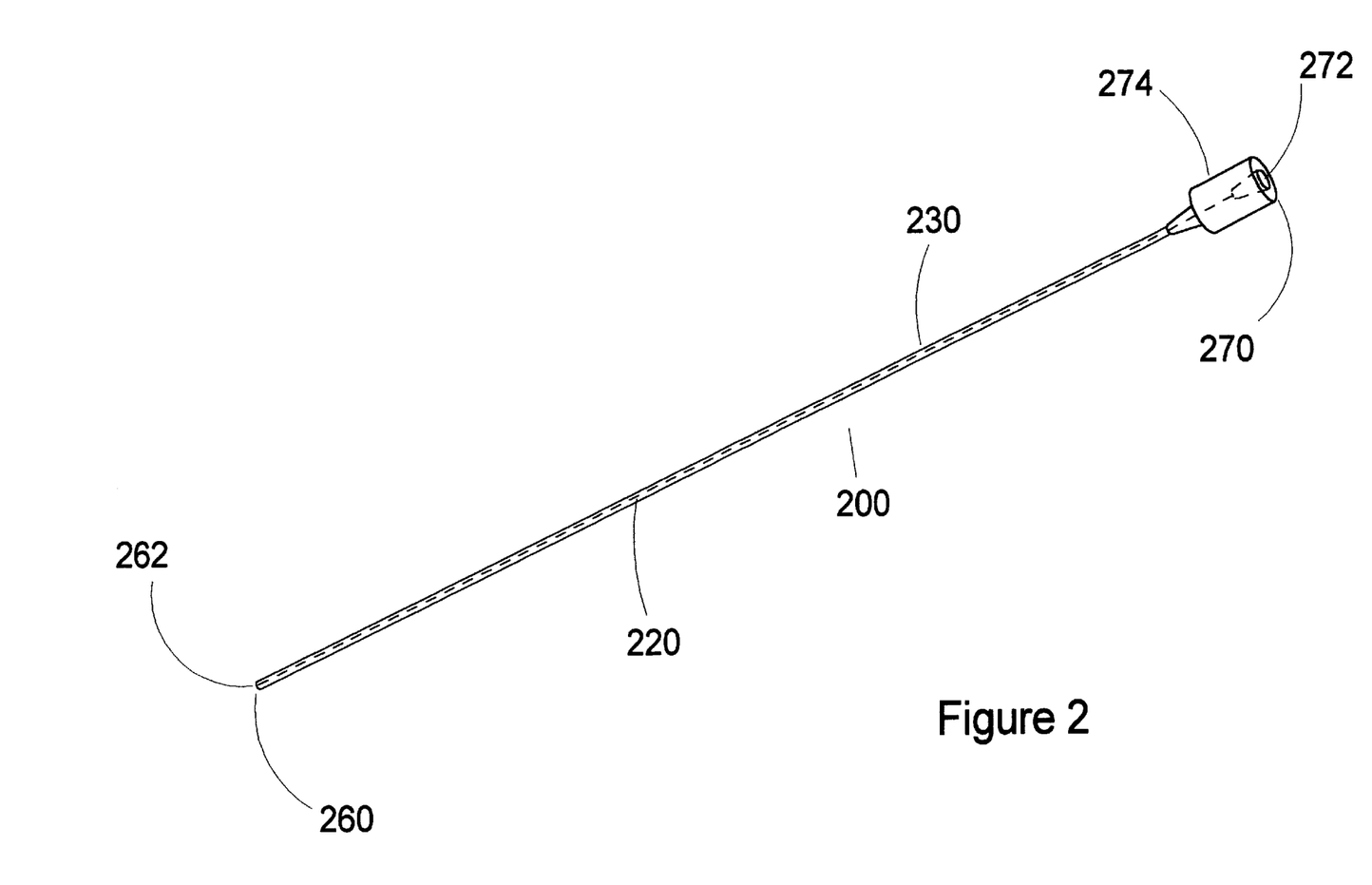
FIG. 2 is a perspective view of the delivery catheter of the invention.

FIG. 2 is a perspective view of the delivery catheter 200 of the invention. Delivery catheter 200 is comprised of a shaft 230 and hub 274. Hub 274 is located at the first end 270 and shaft 230 extends from first end 270 to second end 260. Shaft 230 is preferably polyimide coated glass and hub 274 is preferably plastic. Bore 220 passes through both shaft 230 and hub 274 to connect second opening 262 and first opening 272 allowing the for the passage of drugs to be administered at the selected site. Bore 230 can have a diameter as small as 1 micron. Shaft 230 has a diameter or thickness slightly smaller than passageway 120 so that delivery catheter 200 may be inserted into guide catheter 100.

Figure 3:
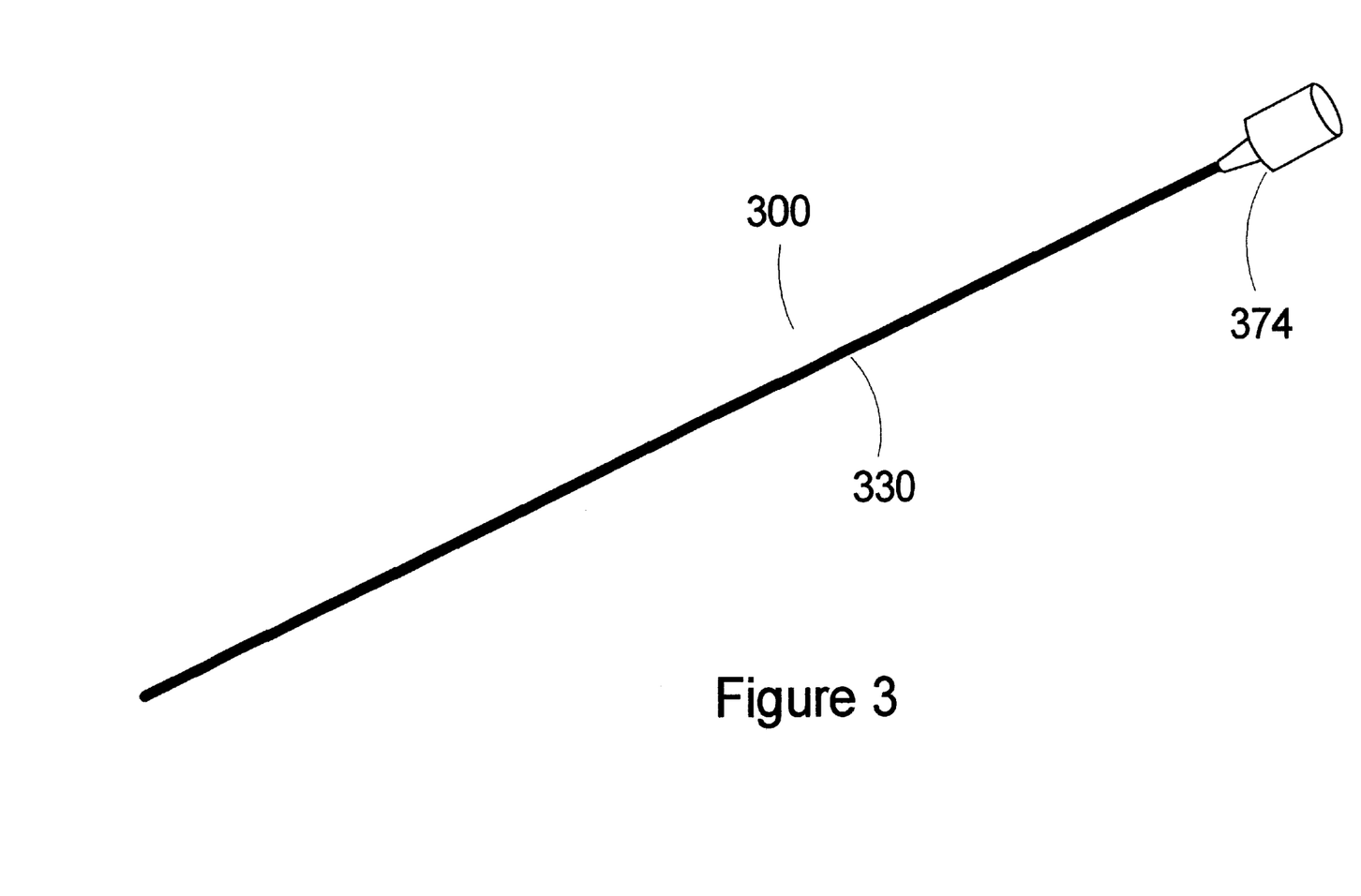
FIG. 3 is a perspective view of the stylet of the invention.

FIG. 3 is a perspective view of the stylet 300 of the invention. Stylet 300 is comprised of a shaft 330 and hub 374. Shaft 330 has a diameter or thickness slightly smaller than passageway 120 so that stylet 300 may be positioned in guide catheter 100 for insertion into a patient's brain. Shaft 330 is preferably stainless steel or a non-ferrous MRI compatible material such as tungsten. Hub 374 is preferably plastic.

Figure 4:
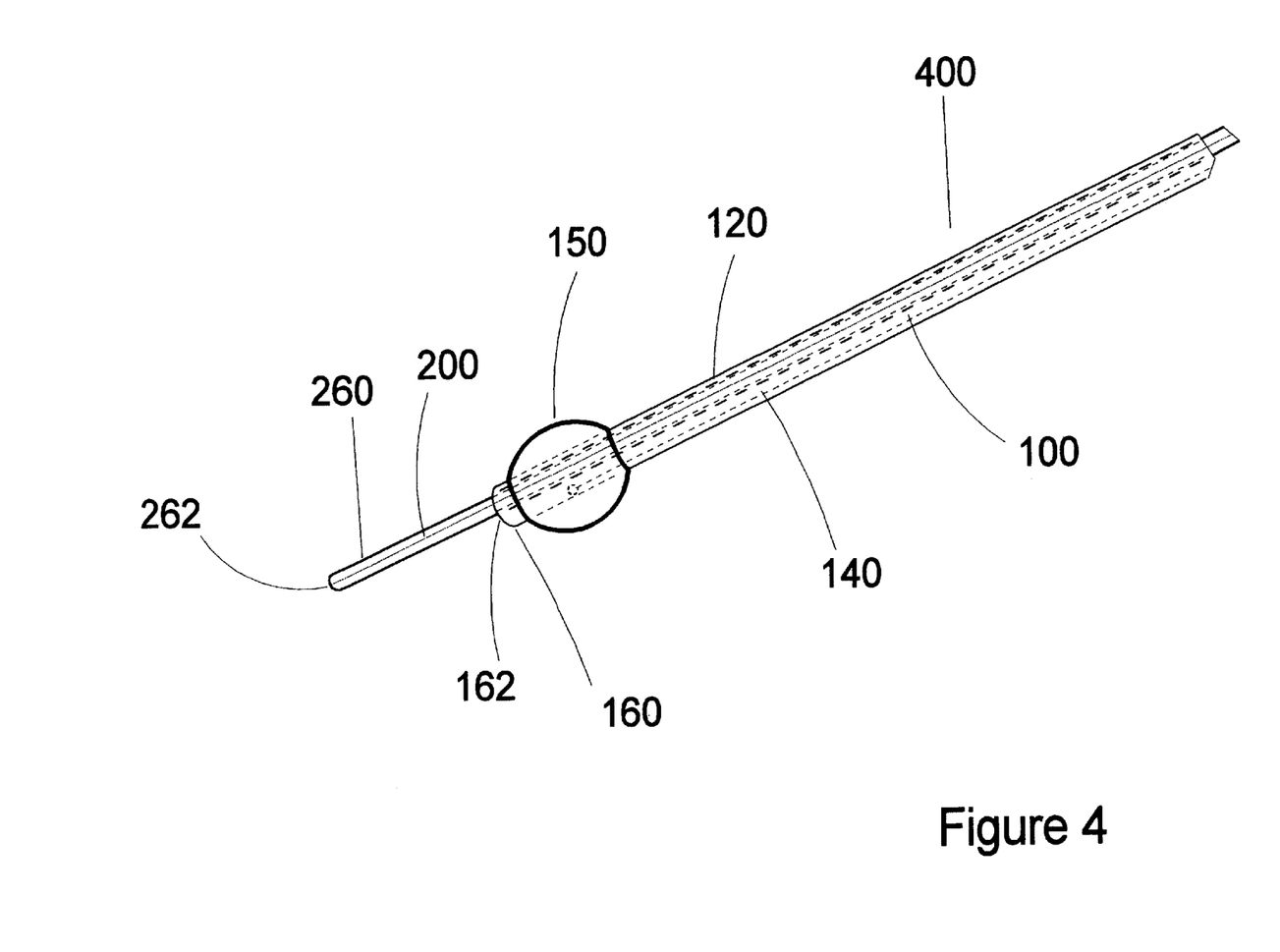
FIG. 4 is a perspective view of the distal end of the assembly having the delivery catheter within the guide catheter and the balloon inflated.

FIG. 4 is a perspective view of the distal end of the assembly 400 having delivery catheter 200 within guide catheter 100 and balloon 150 inflated. When delivery catheter 200 is inserted into guide catheter 100 second opening 262 extends beyond distal opening 162. Balloon 150 is inflated by air forced through lumen 140 and seals or occludes the tract created by the insertion of guide catheter 100 into the brain. Delivery catheter 200 is slightly thinner than passageway 120 so that delivery catheter can pass therethrough without allowing any drugs to flow back out of passageway 120.

Figure 5:
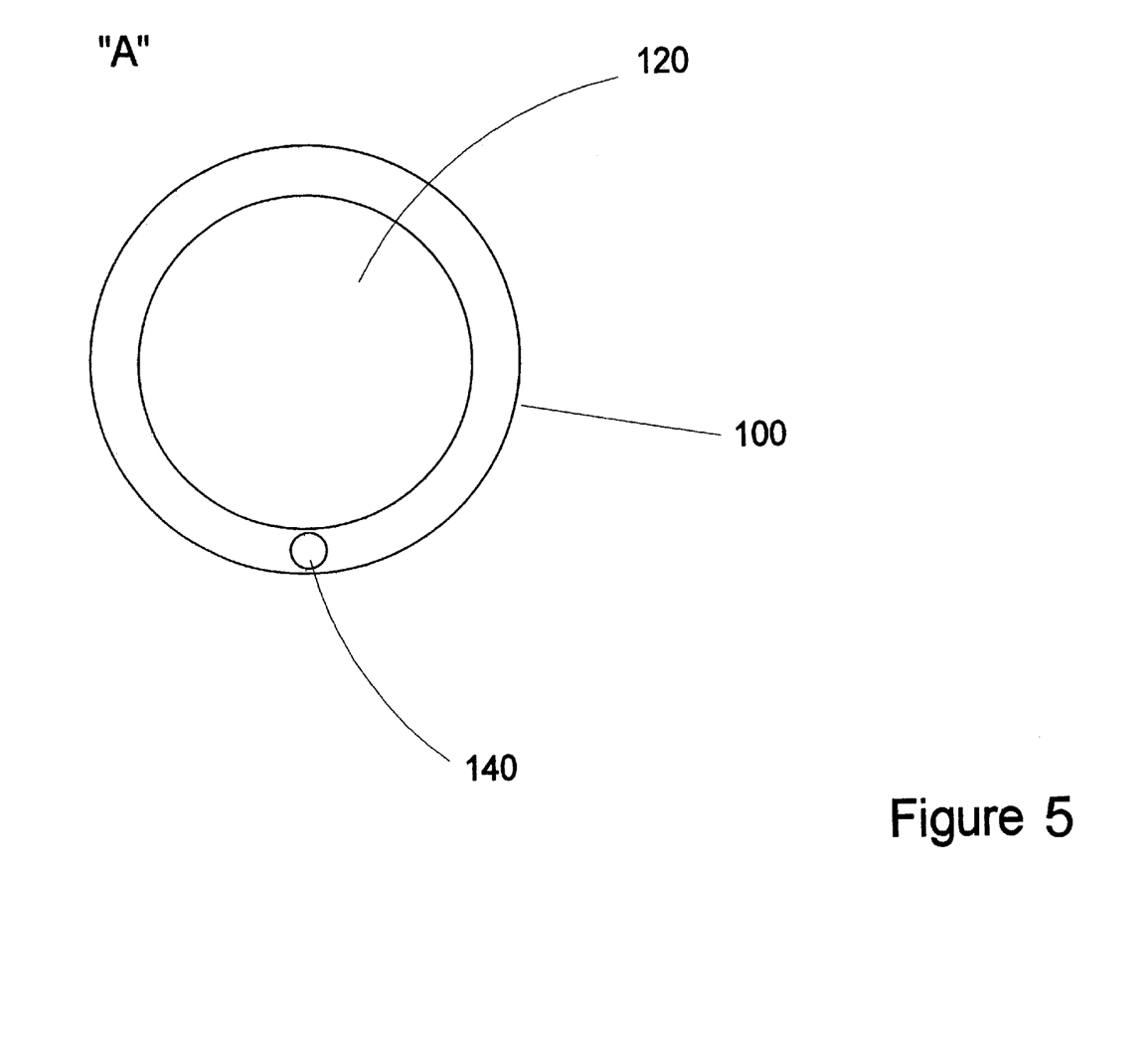
FIG. 5 is a cross section view of the guide cannula of the invention taken along line "A" of FIG. 1.

FIG. 5 is a cross section view of the guide cannula 100 of the invention taken along line "A" of FIG. 1. It depicts the relationship between passageway 120 and lumen 140.

Figure 6:
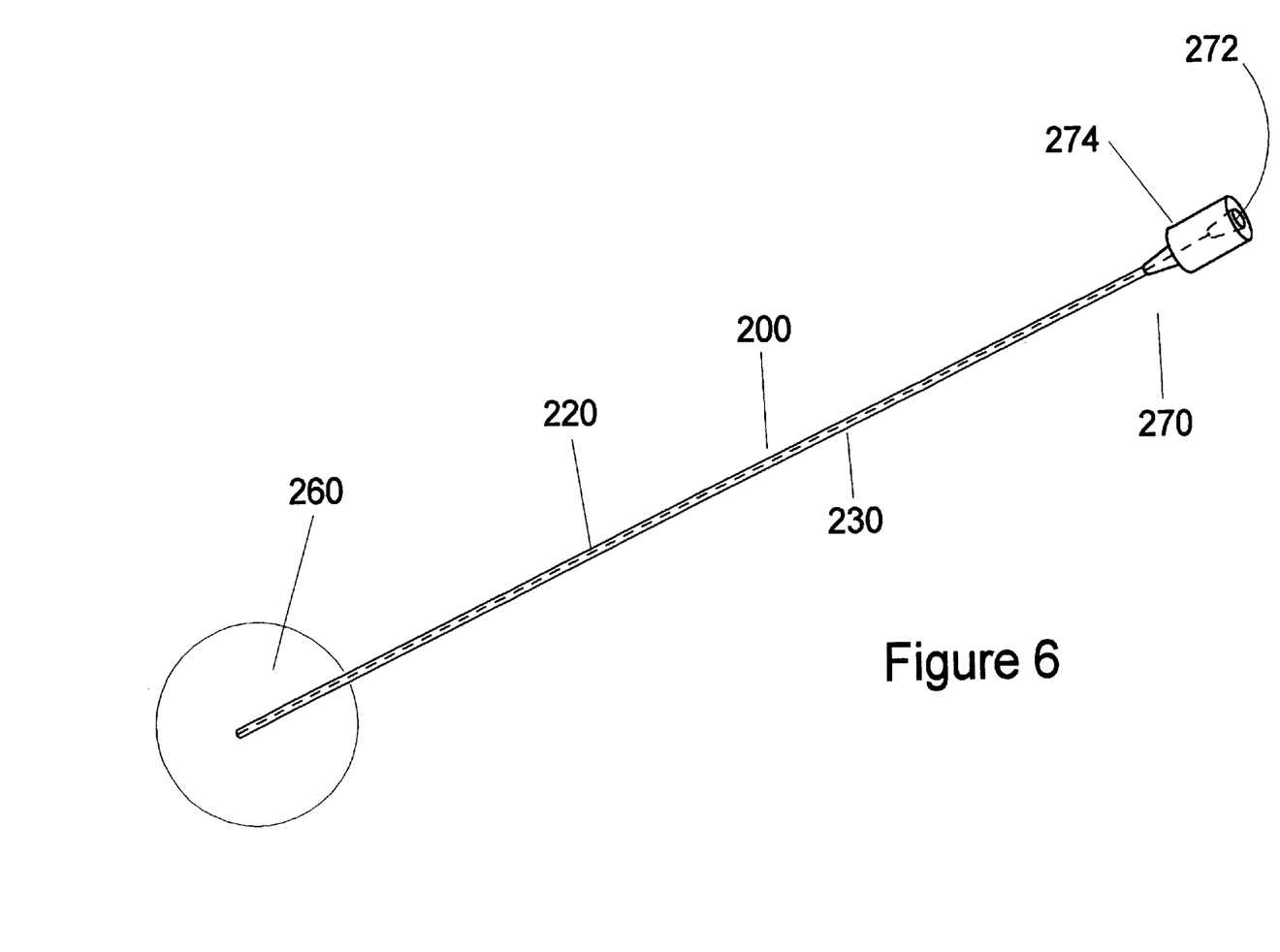
FIG. 6 is a perspective view of an alternative embodiment of the delivery catheter of the invention.
Figure 7:
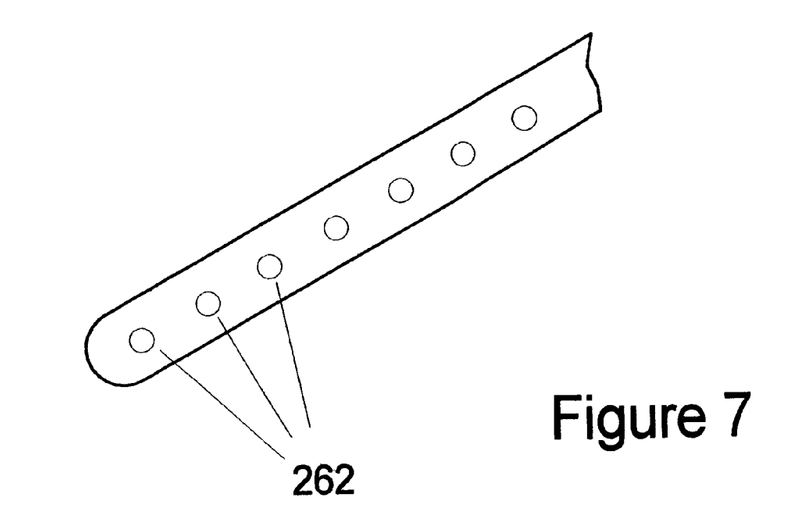
FIG. 7 is a close-up view of the second end of the delivery catheter shown in FIG. 6.

FIGS. 6 and 7 are a perspective views of an alternative embodiment of the delivery catheter 200 of the invention. In this embodiment there are multiple second openings 262 which are arranged along the side of delivery catheter 200. As shown, delivery catheter 200 does not have an opening coaxial with bore 220 though an embodiment could have both coaxial and non-coaxial openings.

Thus, it should be apparent that there has been provided, in accordance with the present invention, an assembly for accurately and effectively delivering drugs to a selected site in a patient's brain that fully satisfies the objectives and advantages set forth above.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A catheter assembly for delivering a drug to a selected site in a patient's brain, comprising:
    intracranial positioning means for providing a passageway within the brain, the intracranial positioning means having proximal and distal ends and a lumen extending from the proximal end to the distal end and terminating at an inflatable balloon;
    a stylet positioned in the passageway for insertion into the brain; and
    a delivery catheter received within the passageway after removal of the stylet, the delivery catheter for delivering the drug to the selected site in the brain, the delivery catheter having a first opening near a first end, a second opening near a second end and an axial bore extending therebetween,
    whereby the balloon can be inflated to seal a tract created during insertion of the intracranial positioning means into the brain so that the drug is fully absorbed by brain tissue at the selected site.

2. The assembly of claim 1 wherein the intracranial positioning means has proximal and distal openings and the passageway extends therebetween.

3. The assembly of claim 2 wherein the second opening of the delivery catheter extends beyond the distal opening of the intracranial positioning means when the delivery catheter is inserted into the passageway.

4. The assembly of claim 3 wherein the second opening of the delivery catheter includes multiple openings for delivering the drug to the selected site.

5. The assembly of claim 4 wherein the multiple openings are non-coaxial with the bore.

6. The assembly of claim 1 wherein the passageway is slightly larger than the delivery catheter to facilitate insertion of the delivery catheter therein.

7. The assembly of claim 1 wherein the balloon is deflatable to enable removal of the assembly from the brain after drug delivery to the selected site.

8. The assembly of claim 1 wherein the delivery catheter includes a hub to facilitate movement of the delivery catheter with respect to the intracranial positioning means.

9. The assembly of claim 3 wherein the second opening is coaxial with the bore.

10. The assembly of claim 1 wherein the stylet is rigid to allow for precise positioning of the intracranial positioning means inside the brain.

11. The assembly of claim 1 wherein the stylet is MRI compatible to allow for precise positioning of the intracranial positioning means inside the brain.

12. A method of delivering a drug to a selected site in a patient's brain, comprising:
    inserting into the brain a guide catheter having proximal and distal ends, proximal and distal openings with a passageway extending therebetween, and a stylet positioned in the passageway, the guide catheter including a lumen extending from the proximal end to the distal end and terminating at an inflatable balloon;
    inflating the balloon by injecting air through the lumen so that a tract created by the insertion of the guide catheter into the brain is sealed;
    removing the stylet from the passageway;
    inserting into the passageway a delivery catheter having a first opening near a first end, a second opening near a second end and an axial bore extending therebetween;
    administering the drug to brain tissue at the selected site by passing the drug through the bore;
    deflating the balloon;
    removing the delivery catheter from the brain; and
    withdrawing the guide catheter from the brain.

13. The method of claim 12 wherein the stylet is removed from the passageway before the balloon is inflated.

14. The method of claim 12 wherein the removing and withdrawing actions are performed simultaneously.

15. The method of claim 12 wherein the the balloon is deflated after the drug has been substantially absorbed by brain tissue at the selected site.

16. The method of claim 12 wherein the second opening of the delivery catheter extends beyond the distal opening after the delivery catheter is inserted into the guide catheter.

17. The method of claim 12 wherein the insertion of the guide catheter into the brain and placement near the selected site is aided by use of magnetic resonance imaging.

18. The method of claim 12 wherein both inserting actions are performed before inflating the balloon.

19. The method of claim 12 wherein the guide catheter is polyimide.

20. A method of ensuring effective drug delivery at a selected site in a patient's brain, comprising:

preparing for insertion into the brain a guide catheter having proximal and distal ends, proximal and distal openings and a passageway extending therebetween, the guide catheter including a lumen extending from the proximal end to the distal end and terminating at an inflatable balloon;

positioning in the passageway a stylet to prevent brain matter from entering the passageway upon insertion of the guide catheter into the brain;

inserting into the brain the guide catheter and stylet;

removing the stylet from the passageway;

inflating the balloon by injecting air through the lumen so that a tract created by the insertion of the guide catheter into the brain is occluded;

inserting into the passageway a delivery catheter having a first opening at a first end, a second opening at a second end and an axial bore extending therebetween;

administering the drug to brain tissue at the selected site by passing the drug through the bore;

deflating the balloon after the drug is substantially absorbed by the brain tissue at the selected site;

removing the delivery catheter from the brain; and withdrawing the guide catheter from the brain.

* * * * *